(12) United States Patent
Nakanishi

(10) Patent No.: US 8,105,346 B2
(45) Date of Patent: Jan. 31, 2012

(54) MEDICAL HANDPIECE

(75) Inventor: Takasuke Nakanishi, Kanuma (JP)

(73) Assignee: Nakanishi Inc., Kanuma-shi (JP)

( * ) Notice: Subject to any disclaimer, the term of this patent is extended or adjusted under 35 U.S.C. 154(b) by 1680 days.

(21) Appl. No.: 11/132,294

(22) Filed: May 19, 2005

(65) Prior Publication Data

US 2006/0263744 A1    Nov. 23, 2006

(30) Foreign Application Priority Data

May 19, 2004    (JP) .................. 2004-149098

(51) Int. Cl.
    *A61B 17/32*    (2006.01)
(52) U.S. Cl. ...................... 606/170; 606/180
(58) Field of Classification Search .............. 433/112,
    433/114, 130, 133, 131, 132, 32, 102–103,
    433/143–144, 165–166; 600/114, 121–125,
    600/136–137, 140–142; 606/170–180, 59,
    606/159, 167, 169; 464/52, 178; 138/112–114;
    74/502.4, 502.6, 500.5, 501.5 R; 604/524–528,
    604/22, 46, 164.09, 164.07; 408/48, 92,
    408/127
See application file for complete search history.

(56) References Cited

U.S. PATENT DOCUMENTS

| | | | |
|---|---|---|---|
| 4,811,736 A | | 3/1989 | Griggs et al. |
| 5,569,256 A | * | 10/1996 | Vaughn et al. .................. 606/80 |
| 5,628,763 A | | 5/1997 | Yazawa et al. |
| 6,213,771 B1 | * | 4/2001 | Fischer ........................... 433/75 |
| 2004/0098006 A1 | | 5/2004 | Nakanishi |
| 2006/0041268 A1 | * | 2/2006 | Shores et al. ................. 606/180 |

FOREIGN PATENT DOCUMENTS

| | | |
|---|---|---|
| EP | 1 155 776 A2 | 11/2001 |
| EP | 1 382 307 A1 * | 1/2004 |
| JP | 8-317930 | 12/1996 |
| JP | 2004-097790 | 4/2004 |

* cited by examiner

*Primary Examiner* — Cris L Rodriguez
*Assistant Examiner* — Edward Moran
(74) *Attorney, Agent, or Firm* — Jason D. Voight

(57) ABSTRACT

The medical handpiece of the present invention has a cutting tool having a flexible shank and a bur provided at the distal end of the cutting tool for cutting an affected area, a tubular sheath for receiving the cutting tool therein, and a handpiece body for detachably holding the proximal end of the cutting tool and transmitting driving force from a drive source to the cutting tool. The sheath and the cutting tool are made flexible for a particular range, with the sheath being plastically deformable and the shank of the cutting tool being elastically deformable. The medical handpiece is further provided with a plurality of bearings arranged in the sheath, first interposed members that are tubular and flexible and arranged proximal to, distal to, and between the bearings, and second interposed members that are tubular and flexible and arranged inside the first interposed members.

6 Claims, 3 Drawing Sheets

MEDICAL HANDPIECE

This application claims benefit to Japanese Patent Application JP 2004-149098, filed May 19, 2004.

FIELD OF ART

The present invention relates to a medical handpiece having a cutting tool that is rotatably driven by power transmitted from a drive source for cutting an affected area.

BACKGROUND ART

Medical handpieces, such as transnasal surgery drills, are conventionally used. This type of handpieces has a cutting tool that is rotatably driven by power transmitted from a drive source, such as a motor, for cutting an affected area. A transnasal surgery drill is used for cutting bone in front of the pituitary gland of a patient by inserting the drill through an expanded nasal cavity of the patient.

The applicant of the present application has filed a patent application regarding a medical handpiece, which is published as JP-2004-97790-A. The medical handpiece disclosed in this publication has a cutting tool having a flexible shank and a bur provided at the distal end of the shank for cutting an affected area. The cutting tool is inserted into a tubular sheath, and a tubular interposed member is interposed between the sheath and the shank of the cutting tool for preventing the shank from contacting the inner surface of the sheath. A handpiece body detachably holds the proximal end of the cutting tool for transmitting driving force from a drive source to the cutting tool. In this medical handpiece, the sheath, interposed member, and cutting tool are made flexible for a predetermined range, with the sheath being plastically deformed, the shank of the cutting tool being elastically deformed, and the interposed member being deformed following the deformation of the sheath and the shank.

In this medical handpiece, the interposed member is in the form of one continuous tubular body that is slightly shorter than a plastically deformable metallic pipe. Due to this structure, when the sheath is flexed for a relatively large angle, the shank of the cutting tool contacts the interposed member at a large pressure for a considerable length. This may cause undesirable vibration of the medical handpiece that deteriorates its operationability, and frictional heat that lowers the durability of the interposed member.

Depending on the affected area to be cut, a plurality of medical handpieces having sheathes of different lengths are used, and correspondingly, a plurality of cutting tools of different lengths are also provided. Medical practitioners have to handle such plurality of medical handpieces, and need to find which cutting tool corresponds to which handpiece, which is bothersome before and during surgery. In addition, the cutting tool, which is detachable for sterilization and cleaning and re-inserted for use, must be held in the handpiece body securely for safety.

SUMMARY OF THE INVENTION

The present invention aims to solve the above problems in the prior art. It is therefore an object of the present invention to provide a medical handpiece wherein vibration is hard to be generated, and heat generated by friction between the interposed member and the shank of the cutting tool is suppressed to a lower level, even when the sheath is flexed for a relatively large angle.

It is another object of the present invention to provide a medical handpiece wherein a cutting tool is easily and correctly matched with a corresponding handpiece body, and secure attachment of the cutting tool to the handpiece body is easily confirmed.

According to the present invention, there is provided a medical handpiece comprising:
a cutting tool having a flexible shank and a bur provided at the distal end of the shank for cutting an affected area,
a tubular sheath for receiving the cutting tool therein, and
a handpiece body for detachably holding the proximal end of the cutting tool and transmitting driving force from a drive source to the cutting tool,
wherein said sheath and said cutting tool are made flexible for a particular range, with said sheath being plastically deformable, and said shank of the cutting tool being elastically deformable,
said medical handpiece further comprising:
a plurality of bearings arranged in said sheath,
first interposed members that are tubular and flexible and arranged proximal to, distal to, and between the bearings, and
second interposed members that are tubular and flexible and arranged inside the first interposed members.

In the medical handpiece of the present invention, a plurality of bearings support the shank of the cutting tool, and the second interposed members arranged proximal to, distal to, and between the bearings act as sliding bearings for the shank. Thus even when the sheath is flexed for a relatively large angle, the shank may contact the second interposed members only at a limited pressure for a limited length, so that the frictional heat generated between the second interposed members and the shank may be suppressed at a low level. Further, around the second interposed members are arranged the first interposed members proximal to, distal to, and between the bearings, and the both interposed members inhibit vibration of the bearings.

According to the present invention, the sheath or the handpiece body has a colored marker provided at a predetermined position, and the cutting tool has a marker of the same color at such a position that the marker on the cutting tool is not seen from outside when the cutting tool is placed in the sheath with its proximal end securely held in the handpiece body, whereas the marker on the cutting tool is seen from outside when the proximal end of the cutting tool is not fully held in the handpiece body.

In the medical handpiece of the present invention, the colored marker on the sheath or the handpiece body is in the same color as the marker on the cutting tool. Thus the cutting tool may be matched with the corresponding handpiece body instantaneously and correctly merely by visual observation of the color matching. Further, the markers also make it easy to detect whether or not the cutting tool is securely held in the handpiece body.

In the medical handpiece of the present invention, vibration of the bearings is suppressed, and heat generated by friction between the second interposed members and the shank of the cutting tool is also suppressed at a low level. Further, the cutting tool is matched with the corresponding handpiece body correctly and reliably.

PREFERRED EMBODIMENTS OF THE INVENTION

Figure 1:
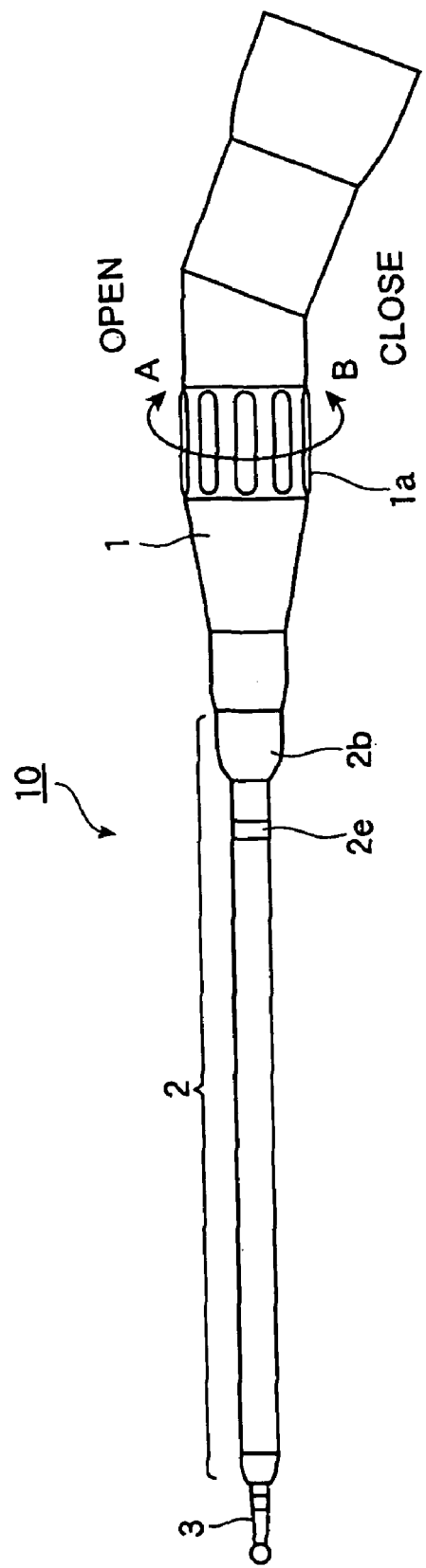
FIG. 1 is a side view of an embodiment of the medical handpiece according to the present invention.

The present invention will now be explained in detail with reference to a preferred embodiment of the invention taken in conjunction with FIGS. 1 to 3.

A medical handpiece according to one embodiment of the present invention, designated as 10, has handpiece body 1, sheath 2 connected to the handpiece body 1, and cutting tool 3 inserted into and placed in the sheath 2. The proximal end of the cutting tool 3 is detachably held in the handpiece body 1, and receives power transmitted from a drive source (not shown). This medical handpiece 10 is designed such that when a medical practitioner holds the sheath 2 with his hand or fingers and applies force thereon, the sheath 2 and the cutting tool 3 may be flexed for a range of not larger than about 30 degrees. Here, the sheath 2 is plastically deformed, while shank 3c (FIG. 2) of the cutting tool 3 inside the sheath 2 is elastically deformed.

Figure 2:
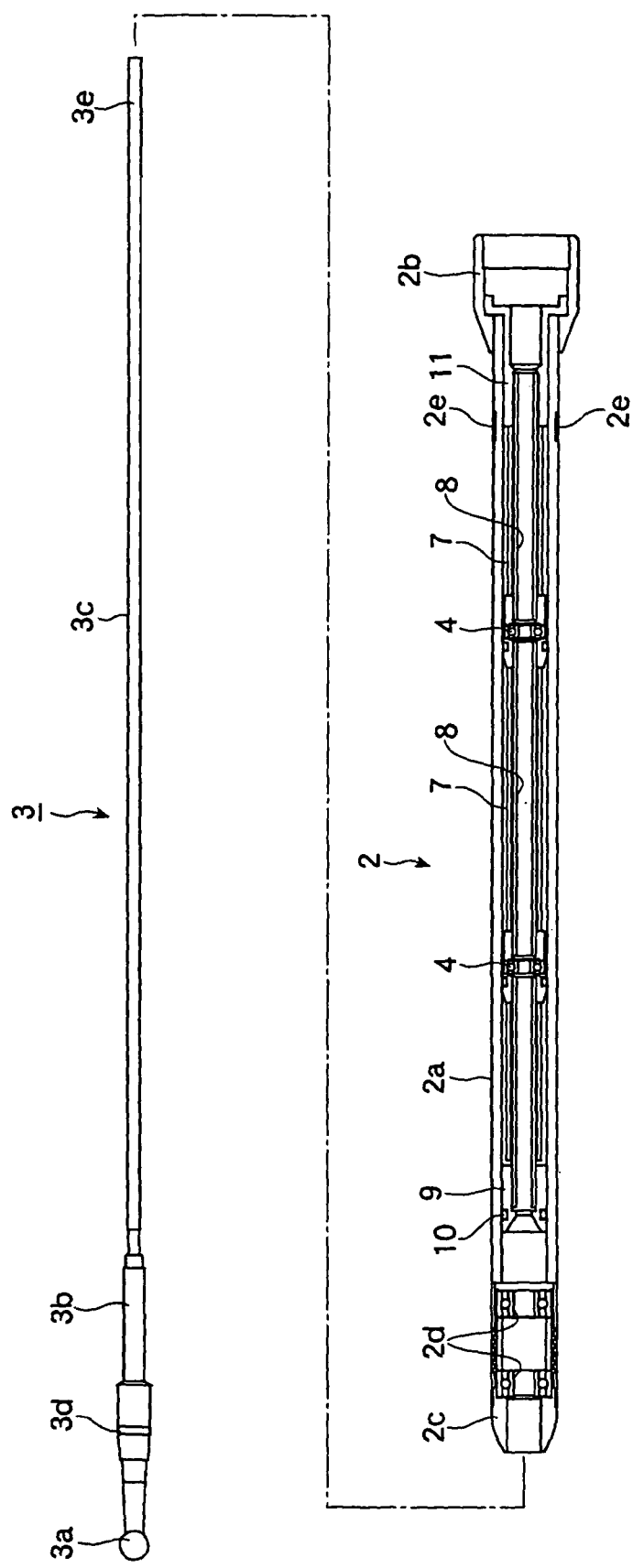
FIG. 2 illustrates the sheath and the cutting tool of the medical handpiece of FIG. 1 in sectional and side views, respectively.
Figure 3:
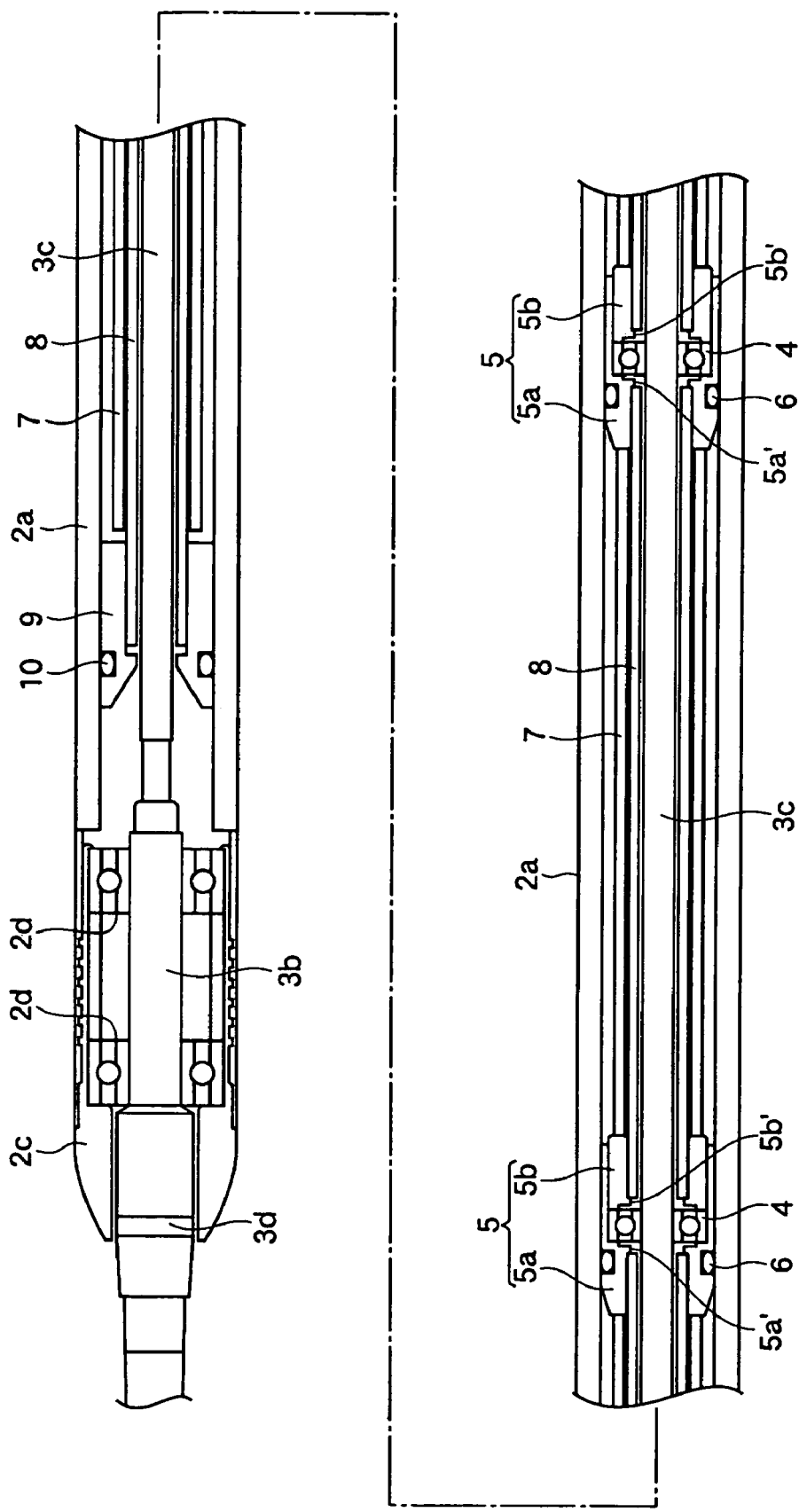
FIG. 3 is an enlarged partial sectional view of the sheath and the cutting tool of the medical handpiece of FIG. 1.

Referring to FIGS. 2 and 3, the sheath 2 includes metallic pipe 2a, connector member 2b, and sheath cap 2c. The metallic pipe 2a may be plastically deformed for a range of not larger than about 30 degrees with respect to its axis, without breaking. The metallic pipe 2a may be made of a metal, such as stainless steel or titanium, and have a relatively thin wall thickness, for example about 0.1 to 0.8 mm. The connector member 2b is provided at the proximal end of the metallic pipe 2a, and has a threaded inner surface for threaded connection with the handpiece body 1. The sheath cap 2c is screwed into the metallic pipe 2a at the distal end thereof. The sheath cap 2c has bearings 2d previously incorporated therein for supporting the distal part of the cutting tool 3. Marker 2e is provided on the sheath 2 at a visible location, for example, around the outer surface of the metallic pipe 2a near its proximal end. This marker 2e is in the same color as marker 3d on the cutting tool 3 as will be discussed later.

Inside the metallic pipe 2a of the sheath 2, a plurality of bearings 4 are arranged. Each bearing 4 is integrally assembled with fixing members 5a, 5b in advance, and inserted into the metallic pipe 2a. The fixing member 5a is fixed by pressure at a predetermined location in the metallic pipe 2a. O-ring 6 is provided between the fixing member 5a and the metallic pipe 2a. The O-ring 6 may be replaced with a packing or a high-viscosity grease. The fixing members 5a and 5b have flanges 5a' and 5b', respectively, protruding radially inwardly from their inner surface. The ends of second interposed members 8 to be discussed later abut the flanges 5a' and 5b', so that displacement of the second interposed members 8 in the thrust direction is prevented.

First interposed members 7 are disposed proximal to, distal to, and between the bearings 4. Inside each first interposed member 7, second interposed member 8 is disposed. The first interposed members 7 are in a tubular form, and contact the fixing members 5a, 5b at both ends to suppress vibration generated at the bearings 4. The first interposed members 7 are made of an elastic material so as to follow the deformation or flexion of the sheath 2, and dimensioned to allow slight displacement in both the radial and thrust directions.

The second interposed members 8 are also made of an elastic material so as to follow the deformation or flexion of the sheath 2, and dimensioned to allow slight displacement in the thrust direction, but not in the radial direction. The second interposed members 8 receive shank 3c of the cutting tool 3 therein. When the sheath 2 is flexed, the shank 3c is likely to contact with the second interposed members 8. For acting as a sliding bearing for the shank 3c upon contact therewith, the second intermediate members 8 are made of a material having both heat resistance and wear resistance, such as a synthetic resin like a fluorocarbon resin.

Stops 9 for interposed members is fixed by pressure in the metallic pipe 2a near the distal end thereof, and stop 11 for interposed members is screwed into the metallic pipe 2a near the proximal end thereof. The stops 9 and 11 for interposed members define, at the distal and proximal end of the metallic pipe 2a, respectively, the limits of displacement of the first and second interposed members 7 and 8 in the thrust direction. The stop 9 for interposed members also functions as a sliding bearing for the shank 3c in some flexed shape of the sheath 2. O-ring 10 is provided between the stop 9 and the metallic pipe 2a. The O-ring 10 may be replaced with a packing or a high-viscosity grease.

The cutting tool 3 has bur 3a at the distal end thereof for cutting an affected area, and the shank 3c extending proximally from the bur 3a via bearing support section 3b. The shank 3c is deformable for a range of not larger than about 30 degree with respect to its axis within the elastic limit, and may be made of a metal such as stainless steel. The bearing support section 3b is in contact with and supported by the bearings 2d of the cap 2c. Marker 3d is provided distal to the bearing support section 3b at a position where the marker 3d is not seen from outside when the cutting tool 3 is placed in the sheath 2 with its proximal end 3e securely held in the handpiece body 1, whereas the marker is seen from outside when the proximal end 3e is not fully held in the handpiece body 1. This marker 3d is in the same color as the marker 2e on the sheath 2.

A plurality of medical handpieces 10 with sheathes 2 of different lengths are provided for various affected areas to be cut, and a plurality of cutting tools 3 of different lengths are provided correspondingly. For sterilizing and cleaning of a medical handpiece in an autoclave or the like, the cutting tool is removed from the sheath, and after the cleaning, the cutting tool is re-inserted into the sheath. Since medical practitioners handle a plurality of medical handpieces, it was extremely bothersome to match a cutting tool with a corresponding medical handpiece before and during surgery. However, with the medical handpiece 10 of the present invention, as discussed above, a cutting tool 3 may be matched with a corresponding medical handpiece correctly and instantaneously, since the sheath 2 is provided with the marker 2e at a predetermined location, and the cutting tool 3 is also provided with the marker 3d of the same color. Further, the markers also make it possible to correctly detect whether or not the cutting tool 3 is securely held in the handpiece body 1.

The handpiece body 1 has twist ring 1a provided in its grip section. The distal end section of the handpiece body 1 distal to the twist ring 1a has threads (not shown) for threaded connection with the connector member 2b of the sheath 2, and the proximal end section of the handpiece body 1 proximal to the twist ring 1a is formed so as to be connected to a driving section such as a motor (not shown). Though not shown in the drawings, the handpiece body 1 also has inside a chucking mechanism, which may be of a conventional structure. This chucking mechanism is structured to be operated by rotating the twist ring 1a with respect to the handpiece body 1 to detachably hold the proximal end 3e of the shank 3c of the cutting tool 3 inserted into the sheath 2. For example, when the twist ring 1a is rotated in the direction of arrow A, the proximal end 3e of the shank 3c is released from the fixing by the chucking mechanism to allow the cutting tool 3 to be detached. When the twist ring 1a is rotated in the direction of arrow B, the proximal end 3e of the shank 3c is fixedly held by the chucking mechanism, and the cutting tool 3 cannot be drawn out.

Next, the function of the medical handpiece 10 with the above structure will be discussed.

With the medical handpiece 10, when the sheath 2 is flexed, the shank 3c of the cutting tool 3 and the first and second interposed members 7 and 8 are elastically deformed according to the deformation of the sheath 2. In this deformed state, when the cutting tool 3 is driven to rotate, the shank 3c rotates with the bearings 4 supporting the shank 3c, so that the shank 3c may be driven to rotate smoothly. In some cases depending on the curved shape of the sheath 2, the shank 3c may rotate partly in contact with the second interposed members 8. Even in this state, the second interposed members 8 function as sliding bearings for the shank 3c to allow smooth rotation of the cutting tool 3.

Also in come cases depending on the curved shape of the sheath 2, the shank 3c may contact the bearings 4 at a relatively high pressure, which may disadvantageously increase vibration generated by the bearings 4. However, with the medical handpiece 10 of the present invention, the first and second interposed members 7 and 8, which are elastic, are arranged to softly contact the fixing members 5a and 5b positioned adjacent to the bearings 4. Thus the vibration of the bearings 4 may be suppressed to a relatively low level.

While the present invention has been discussed with reference to a transnasal surgery drill as an example, the present invention may also be applied to any medical handpieces having a cutting tool with a shank detachably inserted into an elongate sheath of a handpiece.

What is claimed is:

1. A medical handpiece comprising:
  a cutting tool having a flexible shank and a bur provided at the distal end of the shank,
  a tubular sheath receiving the cutting tool therein, and
  a handpiece body detachably holding the proximal end of the cutting tool and transmitting driving force from a drive source to the cutting tool,
  wherein said sheath and said cutting tool are made flexible, with said sheath being plastically deformable and the shank of said cutting tool being elastically deformable, said medical handpiece further comprising:
  a plurality of bearings arranged in said sheath,
  a plurality of first interposed members that are tubular and flexible and arranged proximal to, distal to, and between the bearings, and
  a plurality of second interposed members that are tubular and flexible and each arranged inside each first interposed member to be in partly sliding contact with the shank contained therein when the sheath is flexed.

2. The medical handpiece of claim 1, wherein at least one of said sheath and said handpiece body has a colored marker at a predetermined position, and said cutting tool has a marker of the same color at such a position that the marker on the cutting tool is not seen from outside when the cutting tool is placed in the sheath with its proximal end securely held in the handpiece body, whereas the marker on the cutting tool is seen from outside when the proximal end of the cutting tool is not fully held in the handpiece body, said marker on the cutting tool is an indicator of whether or not the cutting tool is securely held in the handpiece body.

3. The medical handpiece of claim 1, wherein said second interposed members are dimensioned to allow slight displacement in the axial direction, but not in the radial direction.

4. The medical handpiece of claim 1, further comprising:
  a pair of fixing members integrally assembled with each of said plurality of bearings and arranged in said sheath,
  wherein said first interposed members contact said fixing members at their ends to suppress vibration generated at the bearings.

5. The medical handpiece of claim 4, wherein each of said fixing members has a flange protruding radially inwardly from its inner surface, and
  wherein said second interposed members are arranged so that their ends abut said flanges to limit displacement in an axial direction.

6. The medical handpiece of claim 4, further comprising:
  a distal stop fixed near a distal end of the sheath, and a proximal stop fixed near a proximal end of the sheath,
  wherein said first interposed members arranged proximal to and distal to the bearings are arranged between the proximal stop and a proximalmost bearing, and between the distal stop and a distalmost bearing, respectively.

* * * * *